United States Patent
Kabrick et al.

(10) Patent No.: US 7,762,985 B2
(45) Date of Patent: Jul. 27, 2010

(54) BALLOON CATHETER FOR TREATING HARDENED LESIONS

(75) Inventors: Chris R. Kabrick, Bloomington, IN (US); Jeffry S. Melsheimer, Springville, IN (US)

(73) Assignee: Cook Incorporated, Bloomington, IN (US)

(*) Notice: Subject to any disclaimer, the term of this patent is extended or adjusted under 35 U.S.C. 154(b) by 145 days.

(21) Appl. No.: 11/925,252

(22) Filed: Oct. 26, 2007

(65) Prior Publication Data

US 2008/0103443 A1     May 1, 2008

Related U.S. Application Data

(60) Provisional application No. 60/855,899, filed on Nov. 1, 2006.

(51) Int. Cl.
*A61M 31/00* (2006.01)

(52) U.S. Cl. .................................... 604/103.07

(58) Field of Classification Search ............. 604/103.07
See application file for complete search history.

(56) References Cited

U.S. PATENT DOCUMENTS

| | | | |
|---|---|---|---|
| 4,040,413 A | 8/1977 | Ohshiro | |
| 4,581,017 A | 4/1986 | Sahota | |
| 4,787,388 A | 11/1988 | Hofmann | |
| 4,958,634 A | 9/1990 | Jang | |
| 5,308,323 A | 5/1994 | Sogawa et al. | |
| 5,308,356 A | 5/1994 | Blackshear, Jr. et al. | |
| 5,645,529 A | 7/1997 | Fagan et al. | |
| 5,865,801 A | 2/1999 | Houser | |
| 5,947,924 A * | 9/1999 | Liprie | 604/103.07 |
| 6,017,324 A | 1/2000 | Tu et al. | |
| 6,068,611 A | 5/2000 | Loffler et al. | |
| 6,540,734 B1 | 4/2003 | Chiu et al. | |
| 6,679,860 B2 | 1/2004 | Stiger | |
| 2003/0120208 A1* | 6/2003 | Houser et al. | 604/103.04 |
| 2005/0277876 A1 | 12/2005 | Hayden | |

FOREIGN PATENT DOCUMENTS

| | | |
|---|---|---|
| EP | 0829271 | 3/1998 |
| GB | 2370779 | 7/2002 |
| WO | WO97/03604 | 2/1997 |
| WO | WO03/039626 | 5/2003 |

OTHER PUBLICATIONS

International Search Report and Opinion for PCT/US2007/023065.

* cited by examiner

*Primary Examiner*—Nicholas D Lucchesi
*Assistant Examiner*—Jason Flick
(74) *Attorney, Agent, or Firm*—Brinks Hofer Gilson & Lione

(57) ABSTRACT

The present invention provides apparatus and methods for treating vascular conditions, and in particular, hardened or fibrous material in a stenosis. In a first embodiment, the apparatus comprises a catheter having proximal and distal regions and a plurality of balloons segments disposed on the distal region at intervals about a circumference of the catheter. A first set of opposing balloon segments are configured to be inflated at substantially the same time to apply a first pressure on the vascular condition, and then a second set of opposing balloon segments are configured to be inflated at substantially the same time to apply a second pressure on the vascular condition. The plurality of balloon segments may be formed by taking one length of balloon material and affixing the material to an outer surface of the catheter at a plurality of segment dividing locations to separate adjacent balloon segments, or alternatively, by providing multiple separate balloon materials.

20 Claims, 4 Drawing Sheets

BALLOON CATHETER FOR TREATING HARDENED LESIONS

PRIORITY CLAIM

This invention claims the benefit of priority of U.S. Provisional Application Ser. No. 60/855,899, entitled "Balloon Catheter for Treating Hardened Lesions," filed Nov. 1, 2006, the disclosure of which is hereby incorporated by reference in its entirety.

BACKGROUND

The present invention relates generally to apparatus and methods for treating vascular conditions, and more specifically, for treating hardened or fibrous vascular conditions by inflating opposing balloon segments in a sequential manner to apply stresses that facilitate treatment of the fibrous vascular condition.

Atherosclerosis and other occlusive diseases are prevalent among a significant portion of the population. The process that may lead to atherosclerosis begins with the accumulation of excess fats and cholesterol in a blood vessel. Atherosclerotic plaque forms within the walls of the vessel and may block or restrict blood flow through the vessel. The condition commonly affects the coronary arteries, the aorta, the iliofemoral arteries and the carotid arteries. Several serious consequences may result from the restricted blood flow, such as ischemic events and blood clots that may block the artery.

There are various types of athlerosclerotic plaque that may form within the vessel wall. For example, some plaque may impede flow and exhibit a calcified or fibrous nature, while other plaque may be considered "vulnerable plaque." Furthermore, the distribution of atherosclerotic plaque in coronary arteries can have a concentric or eccentric cross-sectional luminal shape.

While vulnerable plaque may develop within the arterial walls without generally narrowing the arterial lumen substantially, occlusive lesions may include calcified or fibrous plaque comprising, for example, necrotic tissue. The necrotic tissue associated with fibrous plaque may cause the arterial wall to progressively weaken, and a rupture of the intima can occur, thereby causing aneurysm and hemorrhage.

Various procedures are known for treating stenoses in the arterial vasculature, such as balloon angioplasty and stenting. During a balloon angioplasty procedure, a catheter having a deflated balloon attached thereto is inserted into a patient's vessel. Once positioned across a constricting lesion, the balloon is then inflated to widen the lumen to partially or fully restore patency to the vessel. After satisfactory widening of the stenosis has been achieved, the balloon is deflated. The catheter then is retracted and removed from the patient's vessel with the balloon in the deflated state. Stenting involves the insertion of a usually tubular member into a vessel, and may be used alone or in conjunction with an angioplasty procedure.

Various problems exist with the use of a conventional balloon catheter having one balloon when treating a fibrous or calcified vascular occlusion. First, a balloon catheter having a single balloon applies radially outward forces in all directions against the occlusion, and while this imposes a radially uniform pressure against the lesion, it may not be effective against treating a hardened or calcified lesion. Moreover, if the fibrous lesion is eccentric, a single balloon cannot direct forces locally against the occluding portion of the lesion.

In view of the foregoing, there is a need for apparatus and methods that effectively treat a vascular condition by applying stresses that facilitate treatment of the vascular condition, and in particular, for hardened or fibrous lesions.

SUMMARY

The present invention provides apparatus and methods for treating vascular conditions, and in particular, hardened or fibrous material in a stenosis. The apparatus comprises a catheter having proximal and distal regions and a plurality of balloon segments disposed on the distal region of the catheter. At least one set of opposing balloon segments are configured to be inflated at substantially the same time to apply a first pressure on the vascular condition.

In a first embodiment, the catheter comprises four balloon segments disposed at substantially equal intervals about the circumference of the catheter, wherein a first set of opposing balloon segments comprise first and third balloon segments disposed approximately 180 degrees apart, and a second set of opposing balloon segments comprise second and fourth balloon segments disposed approximately 180 degrees apart. The first set of opposing balloon segments, i.e., the first and third balloon segments, are configured to be inflated at substantially the same time to apply a first pressure on the vascular condition. Subsequently, the second set of opposing balloon segments, i.e., the second and fourth balloon segments, are configured to be inflated at substantially the same time to apply a second pressure on the vascular condition. In this manner, multiple non-uniform pressures may be imposed upon the vascular condition, and greater pressures may be achieved to facilitate treatment of the vascular condition.

The catheter may comprise a plurality of inflation lumens, wherein each inflation lumen corresponds to a particular balloon segment. The inflation lumens corresponding to the first set of opposing balloon segments may be placed in fluid communication with one another, thereby causing substantially simultaneous inflation of the first set of opposing balloon segments. Similarly, the inflation lumens corresponding to the second set of opposing balloon segments may be placed in fluid communication with one another, thereby causing substantially simultaneous inflation of the second set of opposing balloon segments.

The plurality of balloon segments may be formed by taking one length of balloon material and affixing the material to an outer surface of the catheter at a plurality of segment dividing locations to separate adjacent balloon segments. In this manner, a fluid impermeable membrane is formed to divide and permit independent inflation of the balloon segments. Alternatively, each balloon segment may be formed from its own independent length of balloon material.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
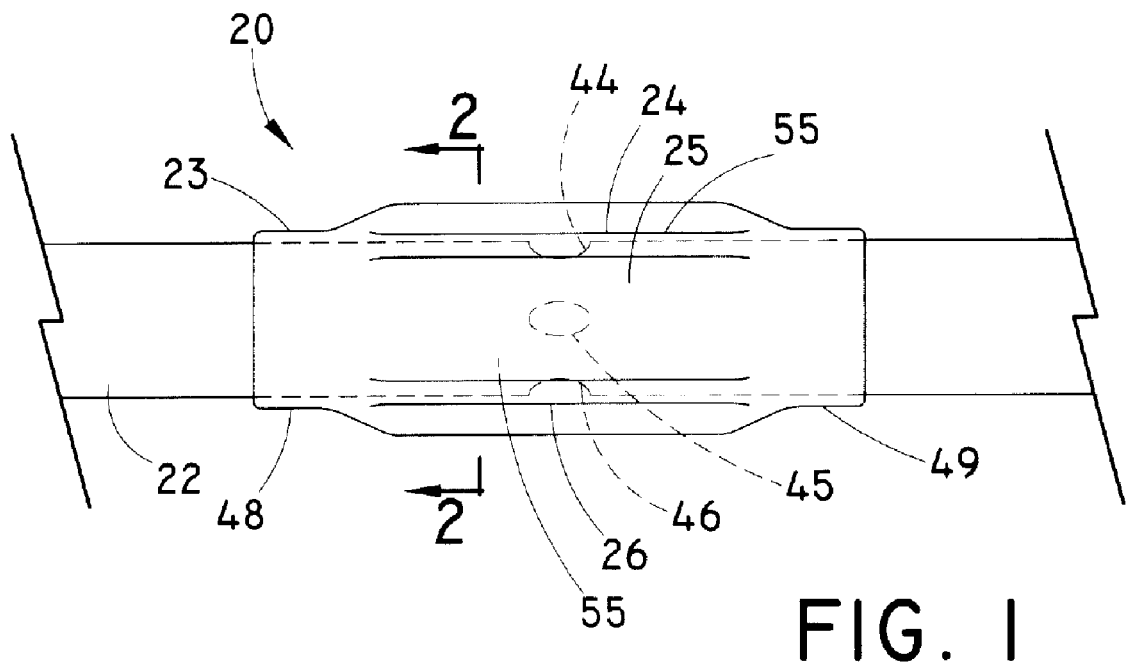
FIG. 1 is a side view of a portion of a balloon catheter having a plurality of balloon segments in a deflated state.

In the present application, the term "proximal" refers to a direction that is generally towards a physician during a medical procedure, while the term "distal" refers to a direction that is generally towards a target site within a patient's anatomy during a medical procedure.

Referring now to FIGS. 1-7, a first embodiment of a balloon catheter having a plurality of balloon segments is described. In FIGS. 1-7, balloon catheter 20 comprises catheter 22 having proximal and distal regions, and a plurality of balloon segments 24-27. It will be appreciated that while four balloon segments 24-27 are depicted in FIGS. 1-7 and two balloon segments 124 and 125 are shown in FIG. 8 below, any number of balloon segments may be employed, e.g., six or eight segments.

Catheter 22 may comprise a flexible, tubular member that may be formed from one or more semi-rigid polymers. For example, the catheter may be manufactured from polyurethane, polyethylene, tetrafluoroethylene, polytetrafluoroethylene, fluorinated ethylene propylene, nylon, PEBAX or the like.

In accordance with one aspect, a plurality of separated balloon segments 24-27 are coupled to an exterior surface of catheter 22. Balloon segments 24-27 may be formed from the provision of four discrete balloon portions that are attached to the exterior surface of catheter 22, or alternatively, may be formed by the provision of one length of balloon material that is adhered to the exterior surface of catheter 22 in selected locations, thereby dividing the balloon length into four separate pockets that form balloon segments 24-27, as explained in greater detail below.

In the embodiment of FIGS. 1-7, one length of balloon material is adhered to the exterior surface of catheter 22 at selected locations to form balloon segments 24-27. Specifically, a single length of balloon material 23 is disposed about the circumference of catheter 22, then affixed at a plurality of segment dividing locations 55 to catheter 22. Segment dividing locations 55 adhere or attach balloon material 23 to catheter 22 to form a fluid-impermeable membrane between balloon segments 24-27, as depicted, for example, in FIG. 2. In particular, balloon material 23 may be affixed to the exterior surface of catheter 22 using an adhesive, such a biocompatible glue, or alternatively, using heat-shrink tubing, heat bonding, laser bonding, welding, solvent bonding, one or more tie-down bands, or the like.

Moreover, balloon segments 24-27 may comprise any number of configurations. In the embodiments shown herein, balloon segments 24-27 comprise a greater longitudinal length than width. Accordingly, segment dividing locations 55 may be substantially longitudinal to ensure full separation of the balloon compartments. Alternatively, balloon segments 24-27 may comprise other shapes, for example, a substantially circular shape, oval shape, or the like.

As shown in FIG. 1, balloon material 23 is preferably further attached to catheter 22 at proximal and distal attachment regions 48 and 49. Balloon material 23 may be attached at these locations using any suitable adhesive, such a biocompatible glue, or alternatively, using heat-shrink tubing, heat bonding, laser bonding, welding, solvent bonding, one or more tie-down bands, or the like. Balloon material 23 may be manufactured from a balloon material, e.g., PEBAX, nylon, Hytrel, Arnitel or other polymers, that is suitable for use during an interventional procedure.

In one exemplary method of manufacture, a laser may be used to bond segment dividing locations 55 to catheter 22. The pattern of bonding may be varied by varying the axial speed of the laser, the rotational speed of catheter 22, and/or by modulating the laser beam. Such manufacturing techniques may be useful for bonding proximal and distal attachment regions 48 and 49, as well as segment dividing locations 55, while avoiding bonding the balloon regions to be inflated, as described below.

Figure 2:
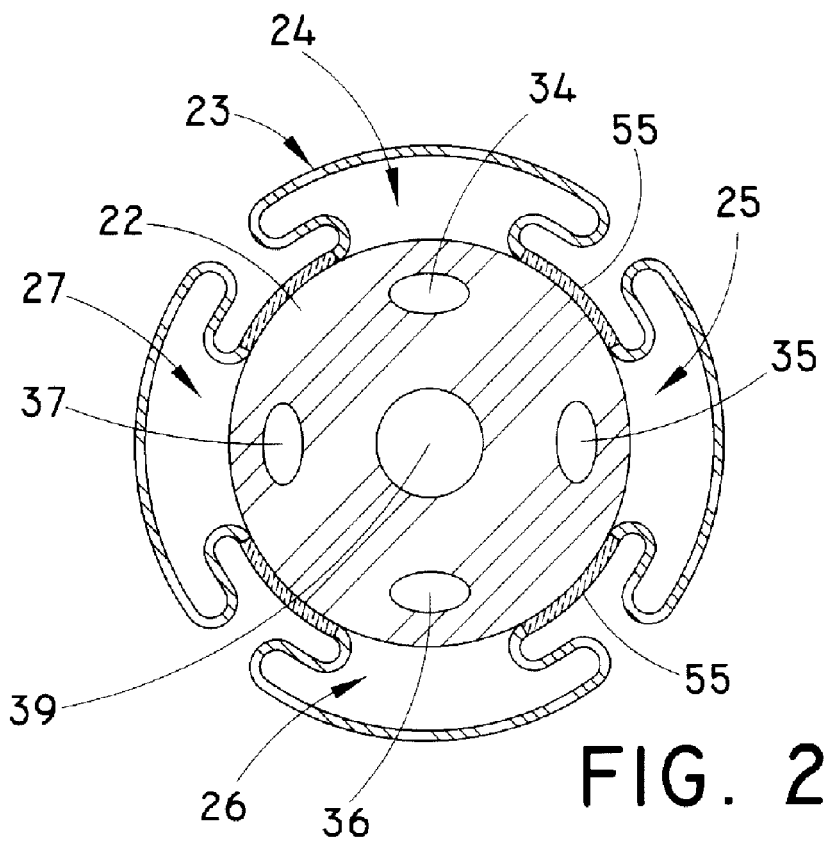
FIG. 2 is a cross-sectional view of the balloon catheter along line 2-2 of FIG. 1.
Figure 3:
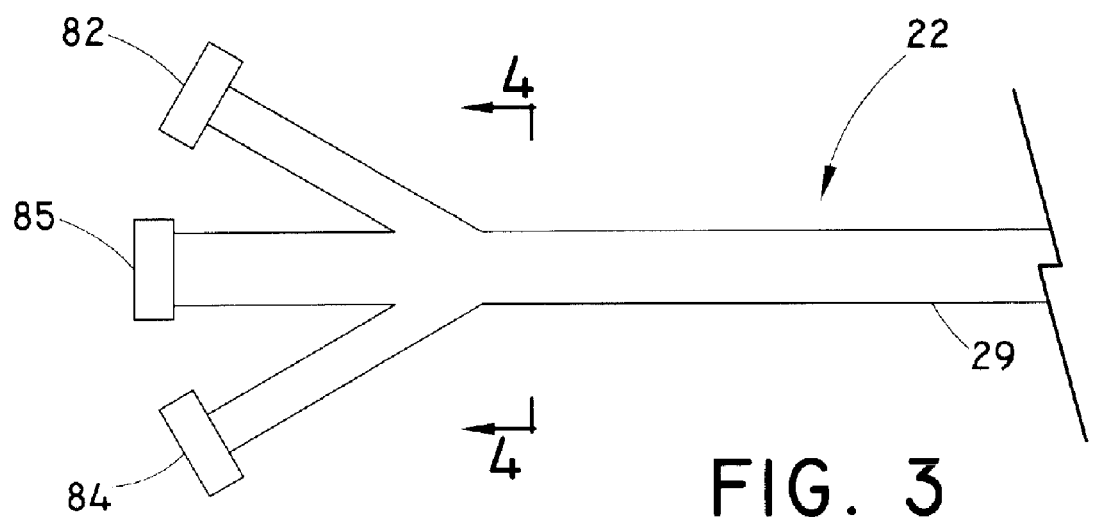
FIG. 3 is a side view of a proximal region of the balloon catheter of FIG. 1.
Figure 4:
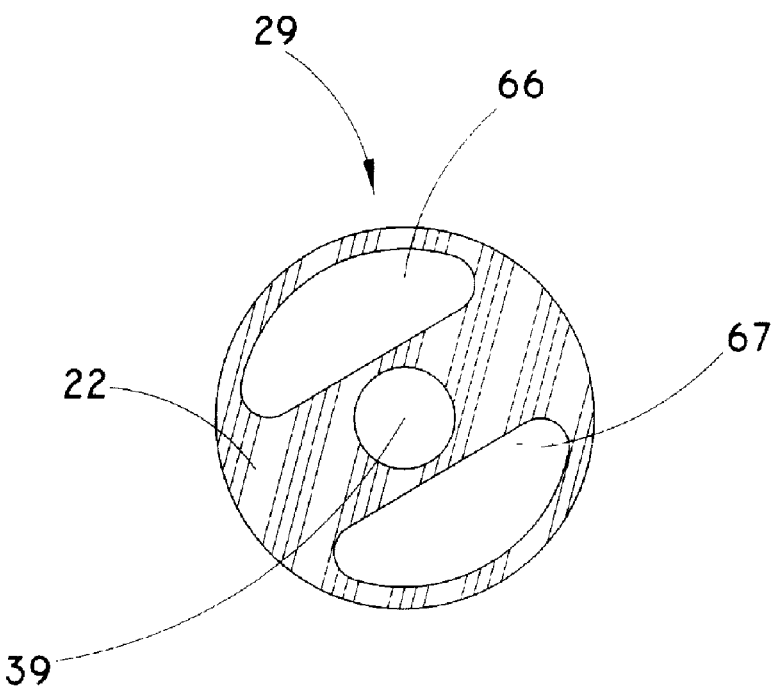
FIG. 4 is a cross-sectional view along line 4-4 of FIG. 3.

Catheter 22 preferably comprises a plurality of inflation lumens 34-37, as shown in FIG. 2. Inflation lumens 34-37 correspond to balloon segments 24-27, respectively. A plurality of side ports 44-47 may be disposed in a lateral surface of catheter 22 to provide fluid communication between inflation lumens 34-37 and the inner confines of balloon segments 24-27, respectively.

It should be noted that inflation lumens 34-37 may be integrally formed with catheter 22, e.g., by extrusion. Alternatively, a plurality of separate inflation lumens may be provided, for example, using multiple pieces of tubing disposed on an external surface of catheter 22, whereby each piece of tubing is placed in fluid communication with a separate balloon segment 24-27.

Further, catheter 22 preferably comprises inner lumen 49 formed therein, as shown in FIG. 2. Inner lumen 49 spans from proximal port 85 (see FIG. 3), through proximal region 29 of catheter 22, and through the distal region comprising balloon segments 24-27. Inner lumen 49 is configured to receive a wire guide and/or other medical components. In one exemplary method of use, a wire guide may be delivered percutaneously to a site of a vascular condition, and balloon catheter 20 may be delivered over the wire guide by placing the distal end of catheter 22 over the wire guide and advancing balloon catheter 20 distally while balloon segments 24-27 are in a deflated state.

In the embodiment of FIGS. 1-7, four balloon segments 24-27 are disposed at substantially equal intervals about a circumference of catheter 22. A first set of opposing balloon segments is defined by first balloon segment 24 and third balloon segment 26, while a second set of opposing balloon segments is defined by second balloon segment 25 and fourth balloon segment 27. As will be explained in greater detail below, inflation of the first set of opposing balloon segments, i.e., segments 24 and 26, at substantially the same time, followed by inflation of the second set of opposing balloon segments, i.e., segments 25 and 27, at substantially the same time, will create stresses on fibrous atherosclerotic plaque to facilitate cracking and/or disruption of the plaque.

In a preferred embodiment, balloon segments 24 and 26 are substantially simultaneously inflated. In order to achieve substantially simultaneous inflation, inflation lumens 34 and 36 preferably are at least partially in fluid communication with one another. In one exemplary embodiment, first inflation port 82 of FIG. 3 may be coupled to proximal inflation lumen 66 of catheter 22 (see FIG. 4), which in turn is later divided into inflation lumens 34 and 36 at a location along catheter 22 that is proximal to side ports 44 and 46. Similarly, second inflation port 84 of FIG. 3 may be coupled to proximal inflation lumen 67 (see FIG. 4), which in turn is divided into inflation lumens 35 and 37 at a location proximal to side ports 45 and 47. Therefore, inflation of fluid via first inflation port 82 and proximal inflation lumen 66 may substantially simultaneously inflate opposing balloon segments 24 and 26, while inflation of fluid via second inflation port 84 and proximal inflation lumen 67 may substantially simultaneously inflate opposing balloon segments 25 and 27, for purposes explained in greater detail below.

Alternatively, inflation lumens 34-37 may span substantially the entire length of catheter 22. First inflation port 82 may be directly coupled to lumen 34, while second inflation port 84 may be directly coupled to lumen 36. A fluid source may be provided to supply fluid in a substantially simultaneous manner to both first and second inflation ports 82 and 84, thereby causing substantially simultaneous inflation of opposing balloon segments 24 and 26. Similarly, lumens 35 and 37 may be directly coupled to third and fourth inflation ports (not shown) to achieve substantially simultaneous inflation of balloon segments 25 and 27, respectively.

Figure 5:
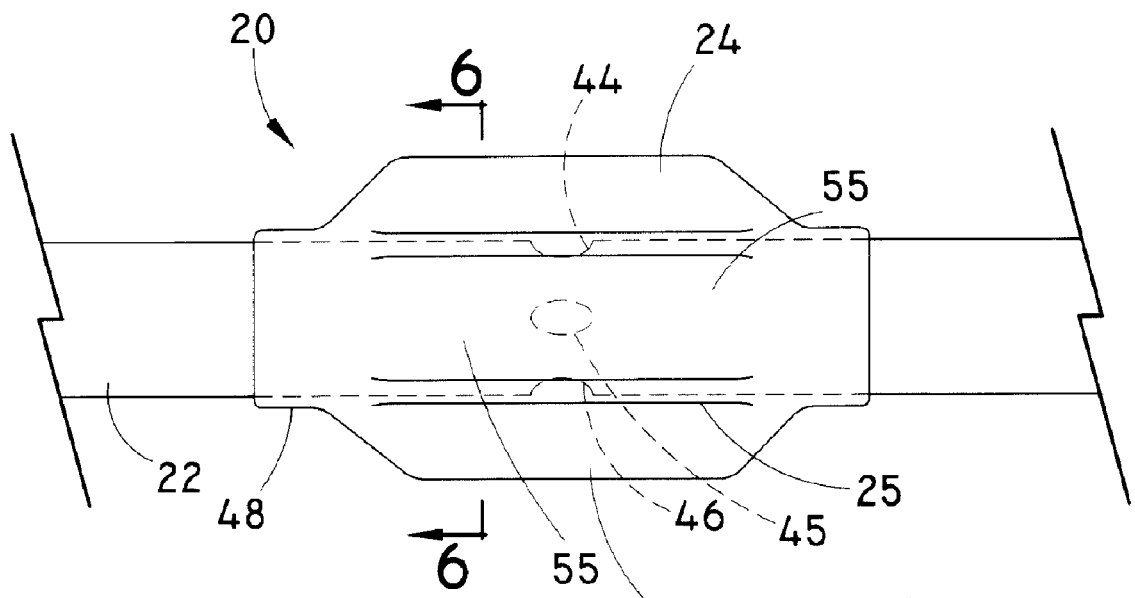
FIG. 5 is a side view of the balloon catheter of FIG. 1 having a first set of opposing balloon segments inflated.
Figure 6:
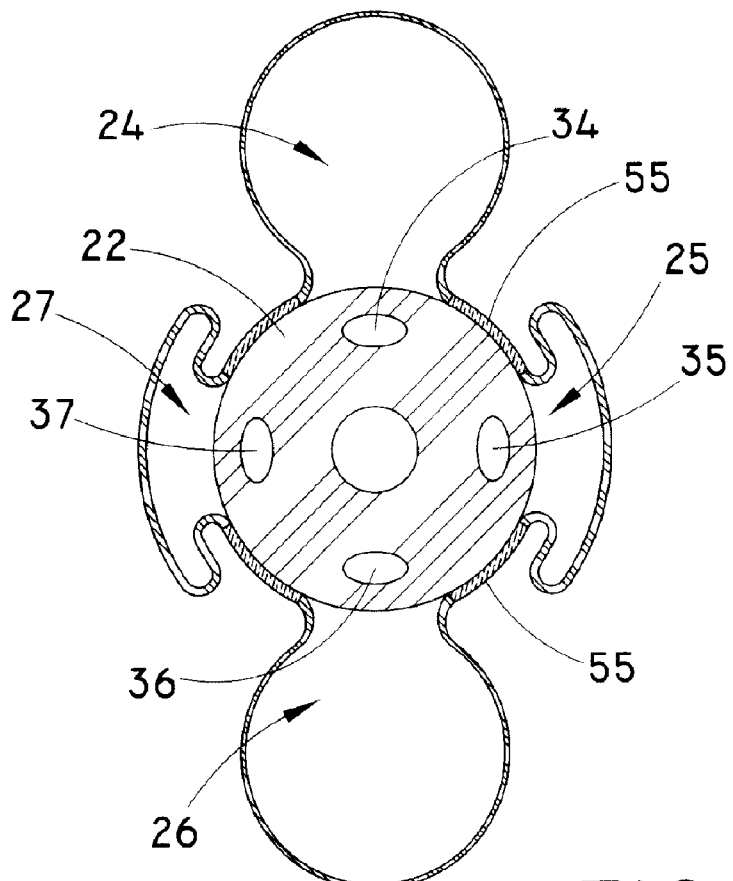
FIG. 6 is a cross-sectional view of the balloon catheter along line 6-6 of FIG. 5.

In an exemplary method of operation, balloon catheter 20 is delivered into a patient's vessel with balloon segments 24-27 in a deflated state, as shown in FIGS. 1-2. When balloon catheter 20 is positioned at a desired location, e.g., within a vascular condition, inflation fluid is provided by inflation lumens 34 and 36 to inflate balloon segments 24 and 26, respectively, as depicted in FIGS. 5-6. At this time, exterior regions of balloon segments 24 and 26 engage a vascular condition and apply a first set of radial stresses for treating the vascular condition.

Figure 7:
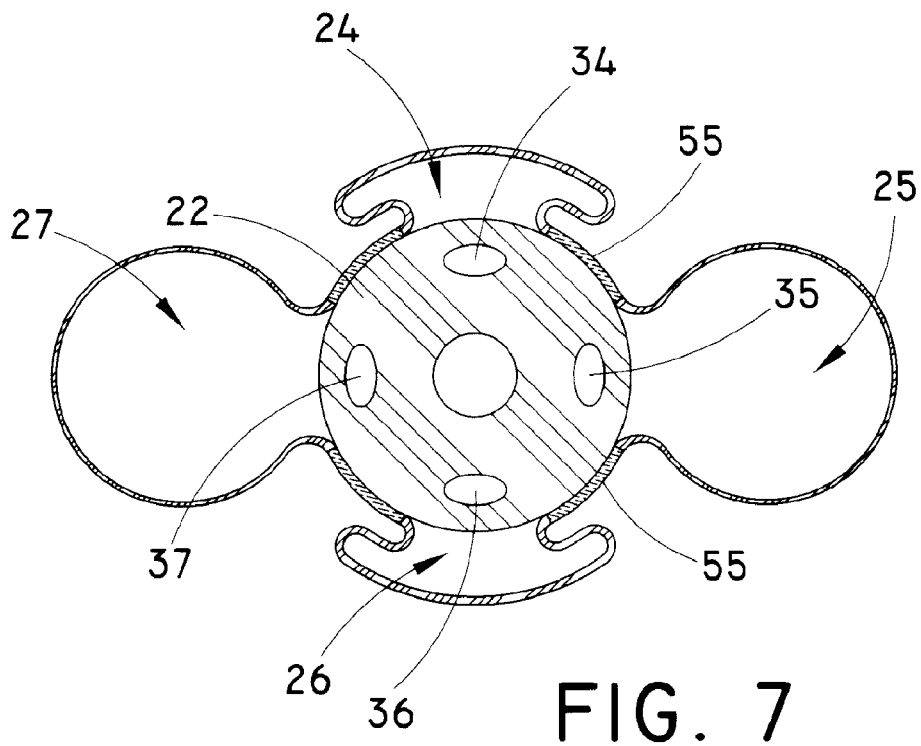
FIG. 7 is a cross-sectional view illustrating inflation of a second set of opposing balloon segments.
Figure 8:
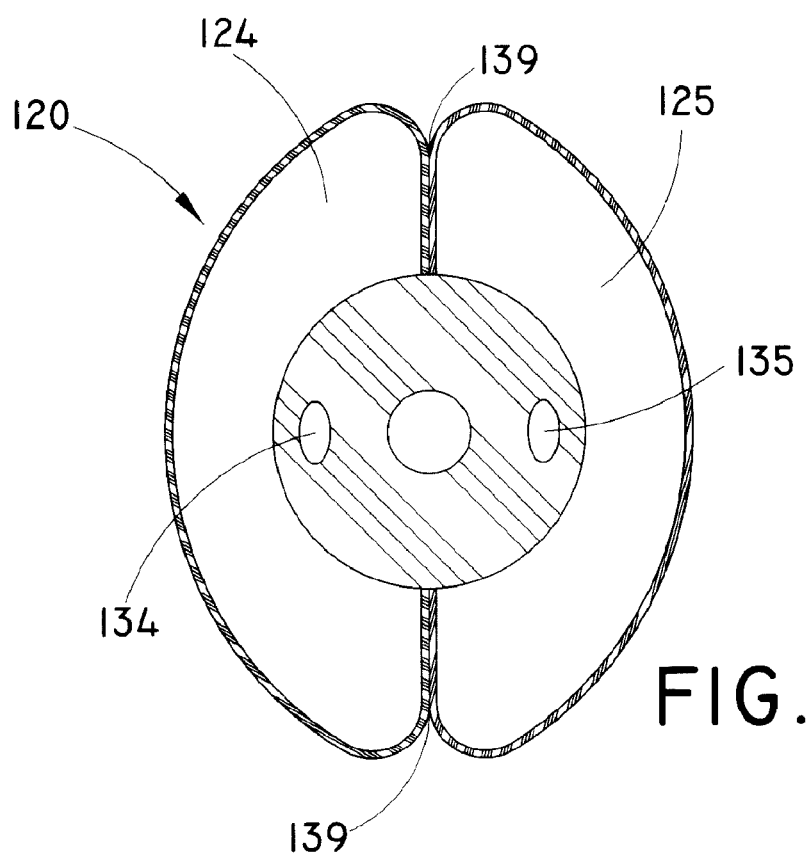
FIG. 8 is a cross-sectional view of an alternative embodiment of the balloon catheter of FIGS. 1-7.

Referring now to FIG. 7, after satisfactory treatment of the vascular condition using radial forces provided by the first set of opposing balloon segments 24 and 26, the opposing balloon segments 24 and 26 are deflated. In a next step, inflation fluid is provided by inflation lumens 35 and 37 to inflate the second set of opposing balloon segments 25 and 27, respectively, as shown in FIG. 7. At this time, exterior regions of balloon segments 25 and 27 engage the vascular condition and apply a second set of radial stresses for treating the vascular condition.

Upon satisfactory treatment of the vascular condition using radial forces provided by opposing balloon segments 25 and 27, the opposing balloon segments 25 and 27 are deflated and balloon catheter 20 may be removed from the patient's vessel with all four balloon segments 24-27 in the deflated state. Alternatively, multiple additional sequences of inflation may be provided, i.e., opposing balloon segments 24 and 26 may be re-inflated, and so forth.

Advantageously, by inflating a first set of opposing balloons, such as balloon segments 24 and 26, and subsequently inflating a second set of opposing balloon segments, such as balloon segments 25 and 27, sequentially opposing stresses may be applied to a vascular condition to facilitate treatment of the vascular condition. Such a technique applies multiple non-uniform pressures upon the vascular condition, which may be useful for cracking or breaking hardened or fibrous material in a lesion. Furthermore, since multiple balloon segments are employed, areas of greater localized pressure may be achieved, as opposed to the use of a single balloon, thereby facilitating treatment of the hardened or fibrous vascular condition.

Referring now to FIG. 8, an alternative embodiment of FIGS. 1-7 is described. Balloon catheter 120 is similar to balloon catheter 20 as described above, with the main exception that two opposing balloons segments are provided instead of four. Specifically, opposing balloon segments 124 and 125 are provided, and may be inflated via inflation lumens 134 and 135, respectively. Optionally, inflation lumens 134 and 135 may be placed in fluid communication with one another to substantially simultaneously inflate balloon segments 124 and 125, as generally described above. Advantageously, by providing two opposing balloon segments 124 and 125, a non-uniform pressure may be generated upon a vascular condition, and a greater localized pressure may be achieved to facilitate treatment of the vascular condition, and in particular, cracking or breaking of hardened or fibrous material in a lesion.

Further, during inflation of balloon segments 124 and 125, gaps 139 are formed between the balloon segments. Gaps 139 provide a flowpath for blood while balloon segments 124 and 125 are expanded to engage an inner wall of a vessel, thereby ensuring that perfusion may be achieved and damage to the patient's vasculature may be reduced.

As noted above, while FIGS. 1-7 generally illustrate one length of balloon material 23 forming multiple, distinct balloon segments 24-27 due to the separation of the balloon segments by segment dividing locations 55, it is within the ambit of the invention that one length of balloon material may be employed for each balloon segment 24-27. Similarly, in the embodiment of FIG. 8, balloon segments 124 and 125 also may be formed from one length of balloon material, or two discrete balloon materials that are separated by segment dividing locations.

While various embodiments of the invention have been described, it will be apparent to those of ordinary skill in the art that many more embodiments and implementations are possible within the scope of the invention. Accordingly, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An apparatus suitable for treating a vascular condition, the apparatus comprising:
    a catheter having proximal and distal regions;
    at least four balloon segments disposed on the distal region at intervals about a circumference of the catheter;
    an inflation lumen corresponding to each balloon segment; and
    a proximal inflation lumen that is distally divided into two inflation lumens corresponding to a first set of opposing balloon segments,
    wherein the inflation lumens corresponding to the first set of opposing balloon segments are in fluid communication with one another via the proximal inflation lumen, thereby causing substantially simultaneous inflation of only the first set of opposing balloon segments while the other balloon segments remain uninflated.

2. The apparatus of claim 1 wherein the inflation lumens corresponding to a second set of opposing balloon segments are in fluid communication with one another, thereby causing substantially simultaneous inflation of the second set of opposing balloon segments.

3. The apparatus of claim 1 wherein the vascular condition comprises a stenosis, wherein the inflation of the first set of opposing balloon segments at substantially the same time creates a non-uniform stress on the stenosis to facilitate treatment of the stenosis.

4. The apparatus of claim 2 wherein the catheter comprises four balloon segments disposed at substantially equal intervals about the circumference of the catheter, wherein the first set of opposing balloon segments comprise first and third balloon segments disposed approximately 180 degrees apart.

5. The apparatus of claim 4 wherein the catheter comprises four balloon segments disposed at substantially equal intervals about the circumference of the catheter, wherein the second set of opposing balloon segments comprise second and fourth balloon segments disposed approximately 180 degrees apart.

6. The apparatus of claim 1 wherein the plurality of balloon segments are formed by taking one length of balloon material and affixing the material to an outer surface of the catheter at a plurality of segment dividing locations to separate adjacent balloon segments.

7. A method for treating a vascular condition, the method comprising:
   providing a catheter having proximal and distal regions, and at least four balloon segments disposed on the distal region;
   delivering the catheter into a vessel with the plurality of balloon segments in a deflated state;
   substantially simultaneously inflating only a first set of opposing balloon segments, while the other balloon segments remain uninflated, to apply a first pressure on the vascular condition, wherein the first set of opposing balloon segments are in the same circumferential plane but not adjacent to one another; and
   substantially simultaneously inflating only a second set of opposing balloon segments, while the first set of opposing balloon segments remains uninflated, to apply a second pressure on the vascular condition.

8. The method of claim 7 wherein the first pressure is substantially the same as the second pressure.

9. The method of claim 7 wherein the vascular condition comprises a stenosis, wherein the inflation of the first set of opposing balloon segments at substantially the same time creates a stress on the stenosis to facilitate removal of atherosclerotic plaque.

10. The method of claim 7 wherein the catheter comprises four balloon segments disposed at substantially equal intervals about a circumference of the catheter, wherein the step of inflating a first set of opposing balloon segments comprises inflating first and third balloon segments disposed approximately 180 degrees apart.

11. The method of claim 10 wherein the step of inflating a second set of opposing balloon segments comprises inflating second and fourth balloon segments disposed approximately 180 degrees apart.

12. The method of claim 7 further comprising:
   providing an inflation lumen corresponding to each balloon segment; and
   selectively inflating each balloon segment by providing an inflation fluid through a respective inflation lumen.

13. The method of claim 12 wherein the inflation lumens corresponding to the first set of opposing balloon segments are in fluid communication with one another, thereby causing substantially simultaneous inflation of the first set of opposing balloon segments.

14. The method of claim 12 wherein the inflation lumens corresponding to the second set of opposing balloon segments are in fluid communication with one another, thereby causing substantially simultaneous inflation of the second set of opposing balloon segments.

15. The method of claim 7 wherein the plurality of balloon segments are formed by providing one length of balloon material and affixing the material to an outer surface of the catheter to separate adjacent balloon segments.

16. Apparatus suitable for treating a vascular condition, the apparatus comprising:
   a catheter having proximal and distal regions; and
   at least four balloon segments disposed on the distal region at intervals about a circumference of the catheter,
   wherein the plurality of balloon segments are formed by providing one length of balloon material and affixing the material to an outer surface of the catheter at a plurality of segment dividing locations to separate adjacent balloon segments; and
   first and second inflation ports, wherein each of the first and second inflation ports is coupled to an inflation lumen corresponding to a first set of opposing balloon segments, wherein a fluid source supplies fluid in a substantially simultaneous manner to both the first and second inflation ports,
   thereby causing substantially simultaneous inflation of only the first set of opposing balloon segments while the other balloon segments remain uninflated.

17. The apparatus of claim 16 wherein the balloon material is attached to the catheter at the plurality of segment dividing locations using an adhesive.

18. The apparatus of claim 17 wherein the balloon material further is attached to the catheter at proximal and distal attachment regions.

19. The apparatus of claim 16 wherein the first set of opposing balloon segments are configured to be inflated at substantially the same time to apply a first pressure on the vascular condition, and wherein a second set of opposing balloon segments are configured to be inflated at substantially the same time to apply a second pressure on the vascular condition.

20. The apparatus of claim 19 wherein the catheter comprises four balloon segments disposed at substantially equal intervals about a circumference of the catheter, wherein the first set of opposing balloon segments comprise first and third balloon segments disposed approximately 180 degrees apart.

* * * * *